United States Patent [19]

Nashner

[11] Patent Number: 5,052,406
[45] Date of Patent: Oct. 1, 1991

[54] APPARATUS AND METHOD FOR MOVEMENT COORDINATION ANALYSIS

[75] Inventor: Lewis M. Nashner, Portland, Oreg.

[73] Assignee: NeuroCom International, Inc., Clackamas, Oreg.

[21] Appl. No.: 7,294

[22] Filed: Jan. 27, 1987

Related U.S. Application Data

[63] Continuation-in-part of Ser. No. 873,125, Jun. 11, 1986, Pat. No. 4,738,269, which is a continuation of Ser. No. 408,184, Aug. 16, 1982, abandoned.

[51] Int. Cl.$^5$ ............................................. A61B 5/11
[52] U.S. Cl. .................................................. 128/782
[58] Field of Search ................ 128/774, 782, 746, 747

[56] References Cited

U.S. PATENT DOCUMENTS 4,738,269  4/1988  Nashner .............................. 128/782

OTHER PUBLICATIONS

Nashner, Sensory Feedback in Human Posture Control; MIT, MVT-70-3; Jun. 1970.
Kates et al., J. Med. Engr.; vol. 4; No. 6, Nov. 1980.
Nashner, Exp. Brain Res.; 30, 1977, pp. 13–24.
Nashner, "Analysis of Stance Posture in Humans"; Chap. 10 of Handbook of Behavioral Neurobiology; vol. 5, Planum Publishing, N.Y., N.Y.; 1981, pp. 527–565.
Nashner et al., Brain Research, 67; 1974, pp. 255–268.
Nashner et al., Exp. Brain Research, 36; 1979; pp. 463–476.
Cardo et al., J. Neurophysiology, vol. 47; No. 2; Feb. 1982; pp. 287–302.
Nashner et al. Brain Research, 150, 1978; pp. 403–407.

Primary Examiner—Kyle L. Howell
Assistant Examiner—J. Hanley
Attorney, Agent, or Firm—Bromberg & Sunstein

[57] ABSTRACT

Methods and Devices are provided for evaluating among the trunk and limbs of the body the distribution of impairments of two types of abilities necessary for posture and equilibrium control: (1) ability to receive and correctly interpret somatosensory orientation and movement information derived from those body and limb parts in contact with supporting surfaces and (2) ability to coordinate the muscular contractions in those body and limb parts in contact with a supporting surface to execute functionally effective postural movements. In accordance with some embodiments, individuals may be classified in accordance with their performance of a Sense Test Procedure and a Motor Test Procedure, which may be implemented using an appropriate displacable support surface arrangement.

7 Claims, 11 Drawing Sheets

APPARATUS AND METHOD FOR MOVEMENT COORDINATION ANALYSIS

This application is a continuation-in-part of Ser. No. 873,125, filed June 11, 1986, now U.S. Pat. No. 4,738,269, for an invention of Lewis M. Nashner, which is in turn a continuation of Ser. No. 408,184, filed Aug. 16, 1982, now abandoned, for an invention of Lewis M. Nashner.

DESCRIPTION

1. Technical Field

This invention relates generally to medical diagnostic devices and methods, and in particular to diagnostic tools for selectively evaluating the distribution and extent of disorders affecting a patient's ability to execute coordinated postured movements.

2. Background Art

There are a wide variety of brain disorders which impair ability to perform posture and motor acts such as standing, walking, and manipulating objects. Examples of such brain disorders include: cerebellar degeneration, Parkinson's disease, traumatic brain injury, multiple sclerosis, and age-related degenerative disorders (see for example Kendal and Schwartz, 1981). Stroke and traumatic head injury can also impair posture and movement controls. And, cerebral palsy and certain forms of developmental learning disorders impair these motor functions. In all of the above instances, the nature and extent of impairment can vary widely, depending on the localization and extent of the brain injury. It is common, for example, that impairment is distributed unequally on the two sides of the body. Within a given body or limb part, muscles exerting force in one direction can be affected differently than those working in the opposite direction. In other instances, impairment can be unequally distributed between sensory and motor aspects of posture and movement control.

Nervous system disorders which impair the brain centers and associated efferent neural pathways controlling activities of the body musculature affect the motor components of posture and equilibrium control. Disorders of this type can result in partial or complete paralysis, or an inability to adequately contract muscles. Muscle paralysis can take the form of one or a combination of slow, weak, or fatiguable contractions, and can be localized to small groups of muscles or widely distributed (see for example Kendal and Schwartz, 1981; Chapters 27 through 29). Alternatively, impairment of brain centers controlling the activities of muscles can result in dyscoordination, contraction of inappropriate muscles or of appropriate muscles in inappropriate timing sequences (Nashner, et al, 1983). In the case of equilibrium control, disorders of postural movement control impair a subject's ability to execute coordinated movements back to an equilibrium position following perturbations therefrom.

Disruption of the brain centers and associated afferent neural pathways from peripheral receptors and muscles, in contrast, disrupts ability to receive and correctly interpret incoming somatosensory information used by the brain to sense muscle forces, joint positions, and orientations of body parts in relation to supporting surfaces. Disorders of this type can result in weak, inappropriate, and inaccurate postural movements and in an inability to maintain an equilibrium position (see for example Kendal and Schwartz, 1981; Chapters 24, 27, and 28).

Presently available clinical methods do not selectively assess both the type and the distribution of sensory and motor disorders impairmenting posture and equilibrium control:

(1) Deep tendon reflexes: Briskly striking the tendon of a muscle produces a brief stretch input exciting stretch receptor organs and, by way of spinal pathways, motor units of the perturbed muscle. Since muscles isolated from central brain efferent controls tend to be overly responsive to brief stretch inputs, physicians use this test to determine the distribution of brain lesions. Deep tendon reflexes, however, do not selectively assess the sensory and motor components of the central brain lesion. Nor are they useful in understanding the functional problems of the patient or predicting the outcome of therapy (Holt, 1966; Milner-Brown and Penn, 1979; Sahrmann and Norton, 1977).

(2) Muscle strength: The individual is asked to exert force against an external resistance, usually the physicians hand. This test is useful to determine the distribution and extent of muscle weakness and paralysis. However, it is well known that both sensory and muscle control abnormalities contribute to weakness and paralysis.

(3) Conscious sense of limb position: The individual with eyes closed is asked to sense the position of a limb as it is passively moved. This method determines the extent of conscious position sense. In the control of posture and equilibrium, however, much of the useful sensory information does not reach consciousness (Nashner and Black, submitted). Thus, the conscious reports of subjects cannot be reliably used to determine the nature and extent of sensory impairment in the posture control system.

(4) Peripheral nerve conduction velocities: There are a number of electro-physiological tests for quantifying the speed of signal conduction within the peripheral motor and sensory nerves. These techniques can determine the distribution and extent of nerve damage contributing to an inability to contract muscle and sense the outcome of motor actions. Assessment of nerve conduction velocities is useful to rule out the possibility of peripheral nerve involvement. This technique, however, cannot separate and characterize sensory and motor impairment due to spinal cord and central brain disorders.

(5) Electromyograms (EMG): The recording of muscle electrical potentials using surface or in-dwelling needle electrodes can be used to identify peripheral neuropathies and number of disorders affecting muscle and muscle contractile mechanisms. Like peripheral nerve assessment, however, EMG's are useful to rule out peripheral causes but cannot separate and quantify the type and extent of sensory and motor impairment of central origin.

(6) Performance of motor tasks: To better characterize the distribution and nature of impaired posture and equilibrium functions, the physician typically observes the patient performing a number of simple motor tasks. Examples of such tasks include finger-to-nose movements, moving the heel of one foot up the shin of the opposite leg, performing rapid alternative rotations of the wrists, walking and performing rapid turns on command, standing and walking heel-to-toe, hopping on one foot, etc. Observations of this type, although valuable, are subjective and therefore cannot selectively assess individual sensory and motor components of posture and equilibrium.

In addition to the standardized clinical assessment methods, devices have been developed to quantify measures human postural sway and postural movements. Several manufacturers currently produce fixed forceplate systems (Kistler Corporation, 75 John Glen Drive, Amherst, N.Y., 14120; Advanced Medical Technology, Inc., 141 California Street, Newton, Mass. 02158). These devices are used to measure the reaction forces exerted by the feet against the support surface. These measures are have been used by researchers and clinicians to quantify the spontaneous sway trajectories of subjects and patients with posture and movement disorders performing simple standing tasks (Arcan, et al, 1977; Baron, et al, 1975; Black, et al, 1978; Coats, 1973; Dietz, et al, 1980; Njiokiktjien and de Rijke, 1972; Japanese authors).

DISCLOSURE OF THE INVENTION

The present invention provides methods and devices for evaluating among the trunk and limbs of the body the distribution of impairments of two types of probabilities necessary for posture and equilibrium control: (1) ability to receive and correctly interpret somatosensory orientation and movement information derived from those body and limb parts in contact with supporting surfaces (hereinafter termed "support surface inputs") and (2) ability to coordinate the muscular contractions in those body and limb parts in contact with a supporting surface to execute functionally effective postural movements. By distribution, I refer to the fact that the sensory and movement disorders described above can each selectively and independently impair functions in some body and limb parts.

The present invention incorporates the following methods: (1) The subject assumes a position of equilibrium while at least two body or limb parts are supported on independent surfaces. (2) Support surface inputs are disrupted from all but one of the supported body or limb parts. (3) The ability of the subject to utilize support surface inputs from each supported body and limb part to maintain the assumed equilibrium position is assessed by measuring the extent of spontaneously occurring displacements from the assumed equilibrium position. (4) The ability of the subject to coordinate postural movements with each supported body or limb part is assessed by imposing brief waveforms of support surface displacement. (5) Steps 1 through 4 are repeated with support surface inputs disrupted from a different combination of all but one of the supported body and limb parts. (6) The distribution of impaired ability to receive and interpret support surface inputs and to coordinate postural movements among the body and limb parts providing postural support is selectively assessed by comparing quantitative measures of spontaneous displacements from the assumed equilibrium position and postural movements.

DESCRIPTION OF SPECIFIC EMBODIMENTS

Figure 1:
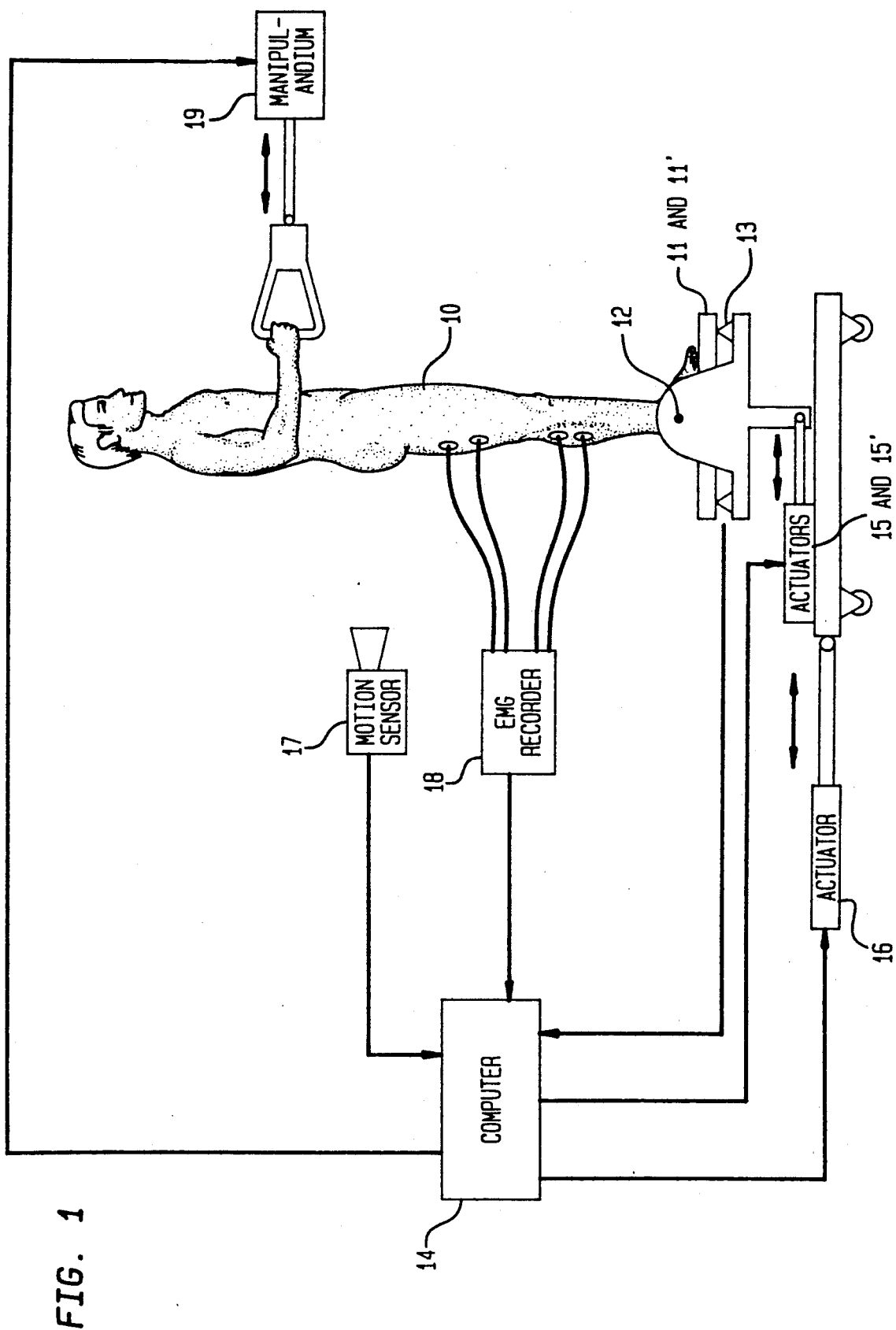
FIG. 1 shows a schematic diagram of the principal components of a preferred embodiment of an apparatus according to the present invention.

Recent investigations describe platform systems which, in addition to measuring surface reaction forces, are movable by hydraulic or electric motor means to unexpectedly perturb a freely standing subject's position in equilibrium (Andres, 1982; Diener, et al, 1982; Diener, et at, 1984; Garfinkel, et al, 1974; Ishida and Imal, 1980; Meyer and Blum, 1978; Nashner, 1970, 1971, 1974, 1976, and 1977; Nashner, et al, 1979; Nashner and Cordo, 1981). Nashner, et al, 1983 uses separate forceplates for each foot to show that the movements and muscle contractile patterns of patients with spastic hemiparesis in response to support surface perturbations were asymmetric. Using EMG's, they are also able to show that asymmetric forces exerted against the support surfaces are caused not by a lack of muscle contractile activity but by changes in the timing and distribution of contractile activity among leg muscles. Using two see-saws, each placed on a separate force measuring platform, Dietz and Berger (1982) show that patients with spastic hemiparesis react asymmetrically to perturbations imposed one foot at a time, whereas normals respond symmetrically with the two feet. These authors, however, have not developed a system for categorizing normal and abnormal postural movements based on measures of the forces exerted by each foot against its support surface, nor do they combine brief support surface perturbations and fixed and sway-referenced support surfaces to systematically disrupt somatosensory orientation information from one foot at a time.

Several investigators have examined postural responses to perturbations in subjects walking. Nashner (1980) imposes brief waveforms of linear vertical and horizontal as well as toes up and toes down rotational support surface perturbations as subjects stepped along a walkway. This study shows that, in the supporting leg during walking, the muscle contractile patterns and forces exerted against the support surface are similar to those seen during in-place standing. Berger, et al (1984) perturbs the posture of subjects walking on a treadmill by abruptly changing the speed of the treadmill belt. They also find postural responses in the support leg to be similar during in-place standing and walking. A further study of posture control during walking was conducted by Nashner and Forssberg (1986), who instructed subjects walking on a treadmill to grip a handle and to exert brief transient pulls on command. Devices have also been developed to measure positions of various body parts during the performance of standing and walking posture and movement control tasks. A computerized infa-red video system allows the positions of a number of markers to be plotted in space (Wattsmart system by Northern Digital Ltd., 415 Phillip Street, Waterloo, Ontario, Canada N2L 3XQ).

According to methods described in the inventor's previous application Ser. No. 873,125, filed June 11, 1986, now U.S. Pat. No. 4,738,269, which is a continuation of Ser. No. 408,184, filed Aug. 16, 1982, now abandoned, support surface inputs useful for controlling one's equilibrium are disrupted by moving the surface supporting that part in functional relation to a quantity related to the subject's displacement from the assumed equilibrium position. Conditions in which a support surface is moved in functional relation to the subject's displacements from equilibrium are called a "sway-referenced" support surface condition. Moving the surface in functional relation to the subject's displacement from equilibrium disrupts the changes in force and orientation of the supported body or limb part in relation to the surface that are correlated with displacements of the subject's center of body mass from the assumed equilibrium position. Under normal conditions, in contrast, support surface inputs are derived from the changes in reaction forces and orientation relative to a fixed support surface that are generated as the body moves away from the assumed equilibrium position. Thus, if the subject incorrectly attempts to rely on support surface inputs, the resulting somatosensory information will inaccurately sense little or no change in body orientation when in fact there are displacements from equilibrium.

By placing the subject in an equilibrium position on a plurality of surfaces, each supporting a different body or limb part, and then sway-referencing all but one of the support surfaces, the subject receives support surface inputs useful for maintaining the assumed equilibrium position from only one body or limb part at a time. For equilibrium to be maintained under these conditions, the brain must first identify the body or limb part receiving the accurate support surface inputs and then use this information as well other visual and vestibular orientation information. By obstructing the subject's vision or by surrounding his field of view with a sway-referenced visual enclosure, however, the above procedure can be repeated in the absence of useful visual orientation information.

The ability of the subject to maintain an assumed equilibrium position while supported with a given combination of fixed and sway-referenced surfaces is quantitatively assessed by measuring the extent of spontaneously occurring displacements of the body from the assumed equilibrium position. These measurements can be made using devices described in the inventor's previous application Ser. No. 873,125, filed June 11, 1986 as well as using devices described in the literature. In one such method, the distribution of vertical and horizontal forces exerted by each supported body part against the surface is measured by incorporating force transducers into the supporting surface (for example, Y. Terekhov, "Stabilometry and some aspects of its applications: a review," *Biomedical Engineering* 11: 12–15, 1976). Alternatively, displacements from the assumed equilibrium position can be measured mechanically by attaching displacement transducers to the body (Nashner, 1970 and 1971) or optically using photographic or video recording techniques (for example Wattsmart System).

In addition to selectively evaluating ability to receive and interpret support surface inputs from body and limb parts one at a time, the present invention can be used to determine the extent to which reception and interpretation of sensory orientation information from a supported body or limb part is impaired. The extent to which sway-referencing disrupts support surface inputs from a given body or limb part can be modified. During sway-referenced conditions, motions of the support surface can be greater than, equal to, or a fraction of the subject's displacement from equilibrium. The term sway-reference "gain" is used to mean the amplitude relation between the measured quantity of body displacement from equilibrium and the functionally related motion of the sway-referenced surface.

When the support surface and visual enclosure movements are equal to the subject's displacement from equilibrium, support surface inputs useful for determining center of body mass displacements from equilibrium are eliminated. When support surface motions are a fraction of the subject's displacement from equilibrium, support surface inputs from the body or limb part in contact with the surface are reduced in amplitude but not completely eliminated. By comparing the ability of the subject to correctly sense position and to minimize spontaneous displacements from the assumed equilibrium position using a fraction of the support surface inputs from one body or limb part, it is then possible to determine the extent to which the subject is able to receive and interpret support surface inputs from the one body or limb part.

Methods for quantitatively assessing the subject's ability to execute the coordinated postural movements necessary to move the body to a position in equilibrium following brief perturbation were disclosed in the inventor's previous application Ser. No. 408,125, filed Aug. 16, 1982, now abandoned. That application included the following method disclosures for eliciting corrective postural movements in a subject maintaining an assumed equilibrium position: (1) brief waveforms of support surface displacement, (2) brief exertion of voluntary force against an external object, and (3) brief waveforms of displacement of an object in the subject's grasp. The previous application also included the following method disclosures for computing parameters of coordination related to the subject's corrective postural movements: (1) measurement of ankle torques (functionally equivalent to support surface reaction forces) exerted by the feet against the support surface, and (2) electromyographic recordings of the contractile activity in selected groups of muscles involved in supporting the subject's position in equilibrium.

As described in the previous application, unexpected displacement of a support surface in one horizontal, linear direction displaces the position of the body center of mass in the opposite direction relative to the points of body support. For example, if the subject is standing on a support surface unexpectedly displaced forward or backward, anteroposterior (AP) sway of the body center of mass in the opposite direction principally about the ankle joints is produced. If the surface horizontal, linear displacement is laterally to one side of the body, the center of body mass sways laterally to the opposite side. If the subject grips a hand-held manipulandum while standing, and on command quickly pulls or pushes in an AP or lateral direction, the subject's center of mass is displaced in the same direction as the self-initiated pull or push. In all of the above instances of perturbation, the subject must contract muscles appropriate to resist the AP or lateral sway displacements of the center of mass and move the body back to the assumed equilibrium position.

The properties of muscular contractions of a given supported body or limb part are quantified during these corrective movements by measuring the distribution of vertical and horizontal forces exerted by the supported part against the surface. Surface reaction forces are used to calculate active response "Latency" and "Strength" parameters for each body part and each direction of perturbation. I develop a system for categorizing active force responses which uses the latency and strength parameters for differing body or limb parts and directions of perturbation. Finally, I establish a set of criteria for distinguishing among normal and abnormal parameters of postural movement for each body part, based on the latency and strength comparisons among parts and perturbation directions.

In parent application Ser. No. 408,184 there was described a second method for computing "Timing" and "Structure" parameters of postural movement coordination during corrective postural movements. This method uses measures of electromyographic (EMG) activity from selected groups of muscles supporting the subject's position in equilibrium to determine which muscles contract and when and in what temporal order they contract. Also established was a set of criteria for distinguishing between normal and abnormal postural movements based on the timing and structure parameters.

Finally, the present invention can be used to assess the extent to which a subject can utilize support surface input information from one body or limb part to control the postural movement activities of other body or limb parts. This type of assessment is important in the subject with asymmetrically distributed impairment, because limbs that function normally utilizing support surface inputs from some body or limb parts can function abnormally when forced to rely on support surface inputs from other parts. By unexpectedly perturbing the assumed equilibrium position of a subject while support surface inputs from all but one supported body or limb part are disrupted by sway-referenced surface conditions, the subject can be forced to rely on support surface inputs from different body or limb parts to initiate the same corrective postural movement. Then, by comparing parameters of postural movement control for different combinations of perturbation and sway-referenced conditions, it is possible to identify for each body and limb part those areas of the body from which support surface inputs can be effectively used to maintain equilibrium.

A preferred embodiment of a device according to the present invention is shown in FIG. 1. The subject (10) stands in a position of equilibrium on two independently movable support surfaces (11 and 11'). Each support surface is rotatable about an axis (12). The subject is positioned on the support surface such that the support surface and ankle joint rotation axes are co-linear. Force sensing means (13) within the two support surfaces and an optional body position and motion sensing means (17) provide measurements functionally related to displacements of the subject from the assumed equilibrium position. An optional electromyographic recording means (18) provides information about the contractile activity of a plurality of leg and trunk muscles. The program means (14), in communication with the measuring means and in accordance with a diagnostic protocol, transmits commands the actuator means which rotate the support surface (15), horizontally translate the support surface (16), and horizontally displace the optional hand-held manipulandum (19).

In a preferred embodiment of a method according to the present invention, the subject (10) assumes an erect standing position in equilibrium with one foot on each of two adjacent and independently rotatable support surfaces (11 and 11'). As shown in greater detail in FIG. 2, each support surface is independently rotatable toes-up and toes-down (21 and 22) about a horizontal axis approximately 2 inches above the surface (12). The subject places the feet so that the ankle joint rotation axis of each is approximately co-linear with the axis of support surface rotations. Support surface rotations are produced independently of each surface by means of the two rotation actuators (15 and 15'). In addition, the two support surfaces can be linearly translated forward or backward together along an axis perpendicular to the rotation axis by means of a separate translation actuator (16).

To selectively remove the somatosensory orientation inputs from one foot at a time, one surface is fixed and the other sway referenced by rotating it in relation to a measured quantity related to the anteroposterior (AP) sway displacements of the subject's center of body mass (hereinafter termed AP stance orientation angle). A quantity related to the AP stance orientation angle is measured by one of several means (13 or 17) described in FIG. 1 and transmitted to the program means (14) which, in accordance with a protocol, then transmits command signals to the two actuator means for rotating the support surfaces (15 and 15') and the actuator means (16) for translating the two support surfaces.

With one support surface sway-referenced and the other fixed, the subject receives support surface inputs useful for maintaining the assumed equilibrium in the AP sway direction only from the leg supported by the fixed surface. The extent to which the subject is able to use support surface input information from the leg supported by the fixed surface is calculated by the program means in accordance with a protocol, and using measurements provided by the one of the measuring means (13 or 17).

In accordance with a protocol implemented by the program means which I call the Sense Test Procedure (STP), spontaneous changes in the AP stance orientation angle are measured and then transmitted to the program means under four separate conditions: (1) both support surfaces fixed, (2) both surfaces sway-referenced, and (3 and 4) one surface sway-referenced at a time. My system for catagorizing the subject's ability to use support surface inputs from each leg is based on differences in the extent of changes in the AP stance orientation angle measurement among the four different STP test conditions. AP stance orientation angle changes for the four test conditions are compared to one another and to a range of values for groups of age-matched normal individuals performing under the same 4 conditions. Comparisons are made using statistical methods well-known in the prior art for identifying significant differences. The categories for classifying abnormal reception and interpretation of support surface inputs performance based on this protocol are outlined in Table I.

stance orientation angle are within the normal range under condition 1 but above the normal range on condition 3 or 4 but not on both, the subject makes use of support surface inputs from one leg but not the other, and the subject is placed in Category B.

Figure 3:
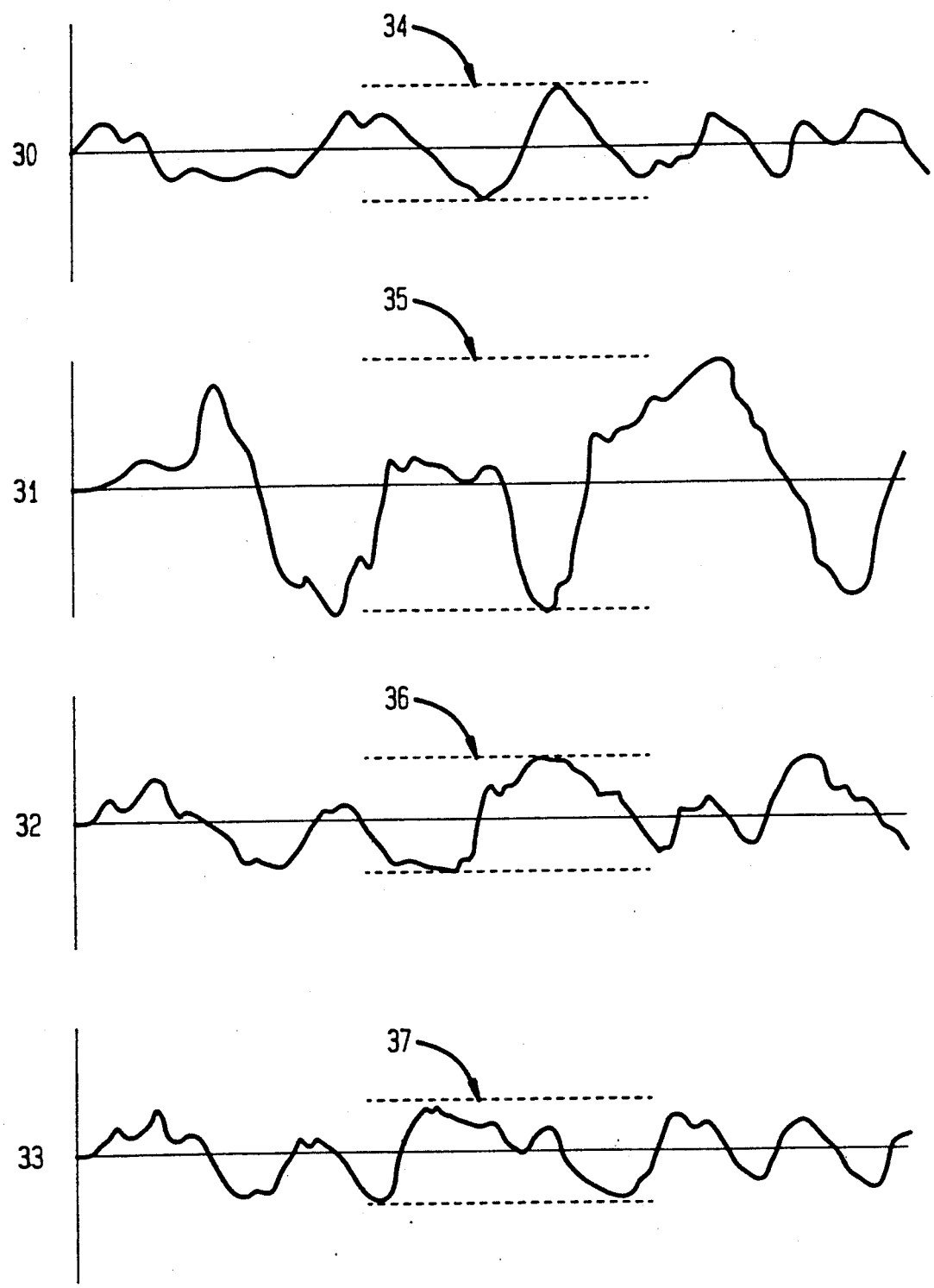
FIG. 3 shows trajectories of spontaneous anteroposterior displacements of the body center of mass typical of normal individuals.

FIG. 3 shows records of AP stance orientation angle typical of a Category N (normal) individual performing under the four test conditions of the STP. Each vertical axis shows forward (up) and backward (down) displacement from the assumed equilibrium position. Each horizontal axis shows the changes in center of mass displacement position over time. The time course of displacements under Test Procedure X for condition 1 is shown in 30, for condition 2 in 31, for condition 3 in 32, and for condition 4 in 33. The extent of displacements from the assumed equilibrium position (dotted lines) are small for condition 1 (34), condition 3 (36), and condition 4 (37), but they are larger for condition 2 (35). The extent of changes in AP stance orientation angle under condition 2 (35) is significantly greater than under condition 1 (34), while angular changes are equal to one another and condition 1 under conditions 3 (36) and 4 (37).

Figure 4:
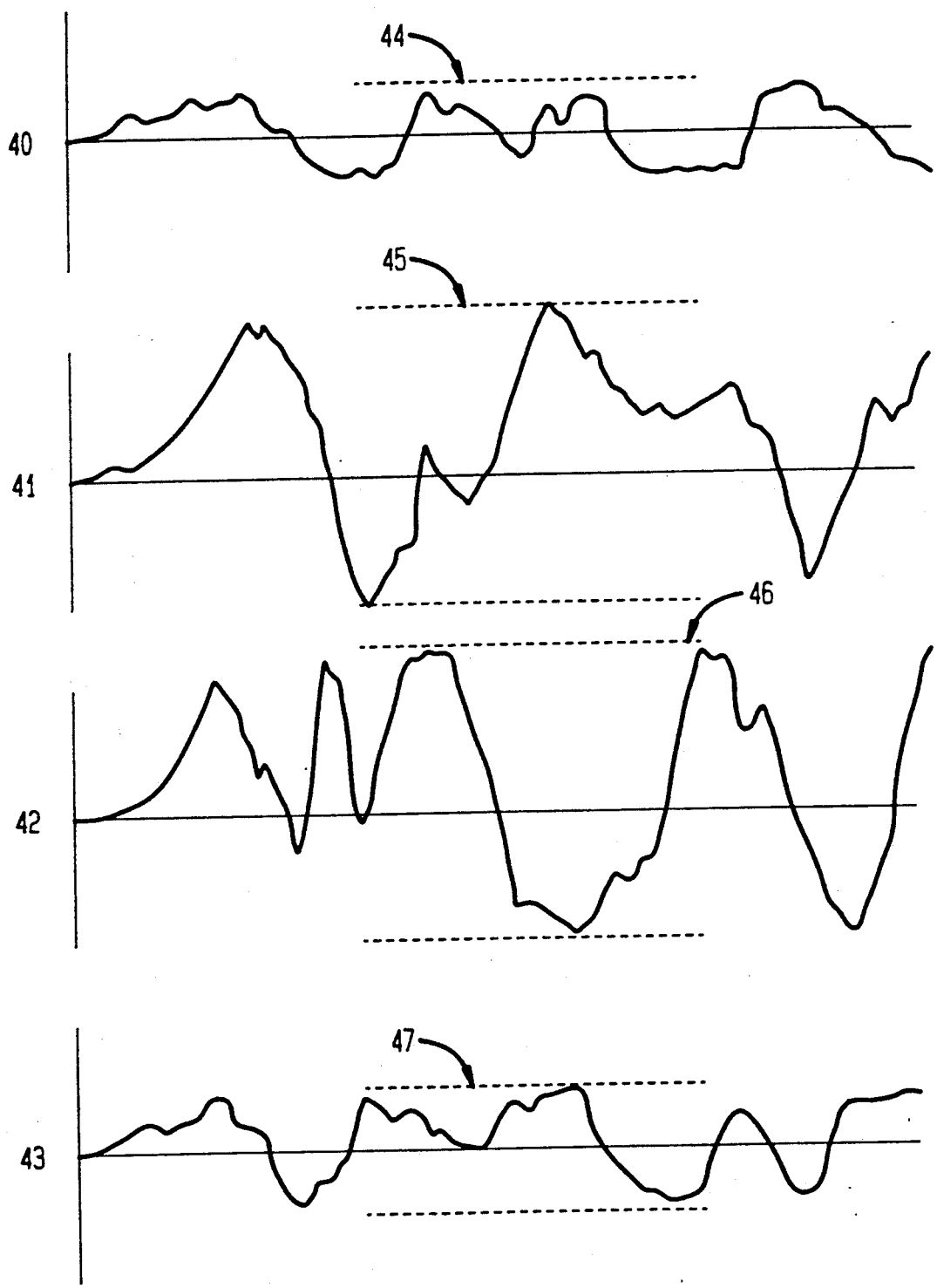
FIG. 4 uses the same format as FIG. 3 to show trajectories of spontaneous anteroposterior displacements of the body center of mass typical of a subject with abnormal ability to receive and interpret somatosensory orientation information from one of the two legs.

FIG. 4 shows records of AP stance orientation angle typical of a Category B (unilateral abnormal) individual. The time course of displacements under Test Procedure X for condition 1 is shown in 40, for condition 2 in 41, for condition 3 in 42, and for condition 4 in 43. The extent of displacements is similar to that of normal individuals for conditions 1 (44), condition 2 (45), and condition 4 (47). The extent of displacements, however, is significantly larger than normal for condition 3 (46). In this individual, the extent of changes in AP stance

TABLE I

CATEGORIES FOR NORMAL AND ABNORMAL RECEPTION AND INTERPRETATION OF SUPPORT SURFACE INPUTS

| SENSE TEST PROCEDURE SENSE CATEGORIES | CHANGES IN AP STANCE ORIENTATION ANGLE COMPARED TO | | | | |
|---|---|---|---|---|---|
| | Age-matched Normals | | | | |
| | Cond 1 | Cond 2 | Cond 3 | Cond 4 | Other Test Conditions |
| A. Bilateral Abnormal | >NORM | >=NORM | >NORM | >NORM | 2 >= 1<br>1 = 3 = 4 |
| B. Unilateral Abnormal (Leg 1) | =NORM | =NORM | >NORM | =NORM | 2 > 1<br>3 > 4<br>2 >= 3 |
| B. Unilateral Abnormal (Leg 2) | =NORM | =NORM | =NORM | >NORM | 2 > 1<br>4 > 3<br>2 >= 4 |
| N. Bilateral Normal | =NORM | =NORM | =NORM | =NORM | 2 > 1<br>1 = 3 = 4 |

Legend:
NORM parameter value range for age-matched normals
1,2 etc parameter value on test condition 1, 2 etc
= substantially equivalent parameter values
> parameter value substantially greater than
>= parameter value equal to or substantially greater than As shown in Table I, a subject is placed in category N (normal) if the extent of changes in AP stance orientation angle are substantially the same under conditions 1, 3 and 4 and within the range established for age-matched normals under all four conditions. Subjects in this category receive and correctly interpret support surface inputs equally well with either one or both of the two legs. A subject is placed in category A if the extent of changes in AP stance orientation angle are substantially above normal range under conditions 1, 3, and 4. Subjects in this category are impaired in their ability to receive and correctly interpret support surface inputs from both legs. If the extent of changes in AP orientation angle under condition 3 (46) is above the normal range and is larger than under condition 4 (47).

The ability of muscles of a given body or limb part to contract with speed, strength, and coordination appropriate to produce effective postural movements is assessed separately for each leg by a protocol, implemented by the program means, which I call the Motor Test Procedure (MTP). Brief horizontal, linear displacements of the support surface in one direction perturb the position of the center of body mass from the equilibrium position in the opposite direction.

Figure 5:
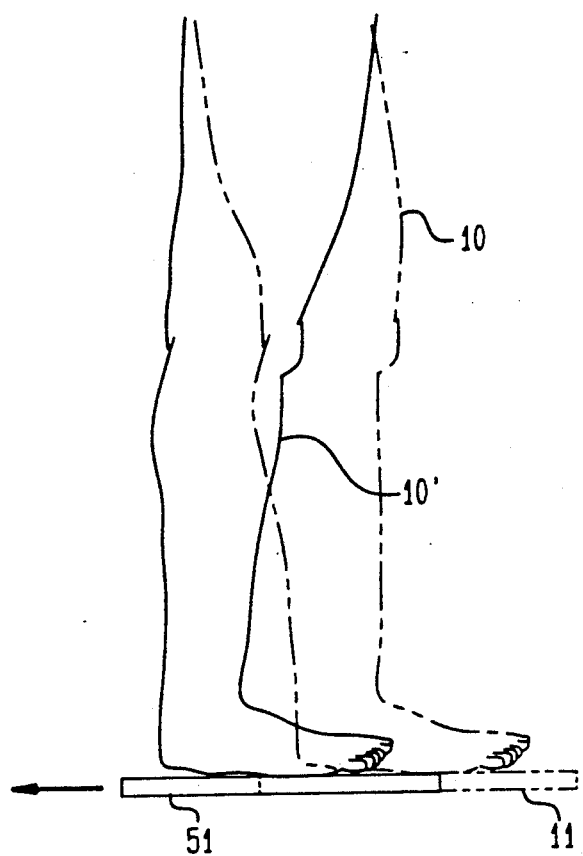
FIG. 5 shows a side view of a subject maintaining an assumed equilibrium position on a support surface prior to and following a backward horizontal, linear displacement of the support surface.

FIG. 5 shows a side view of a subject maintaining an assumed equilibrium position on a support surface prior to and following a backward horizontal, linear displacement of the support surface. Dotted lines show position of the subject (10) and the support surface (11) prior to the horizontal, linear displacement. Solid lines show the position of the subject (10') and the support surface (51) following the backward horizontal, linear displacement.

To maintain standing balance, the subject must perform a rapid postural movement back to the assumed equilibrium position. The properties of the resulting postural movements are assessed by measuring the forces exerted by the supported body and limb parts against the support surface and by the muscle contractions associated with these rapid postural movements.

Figure 6:
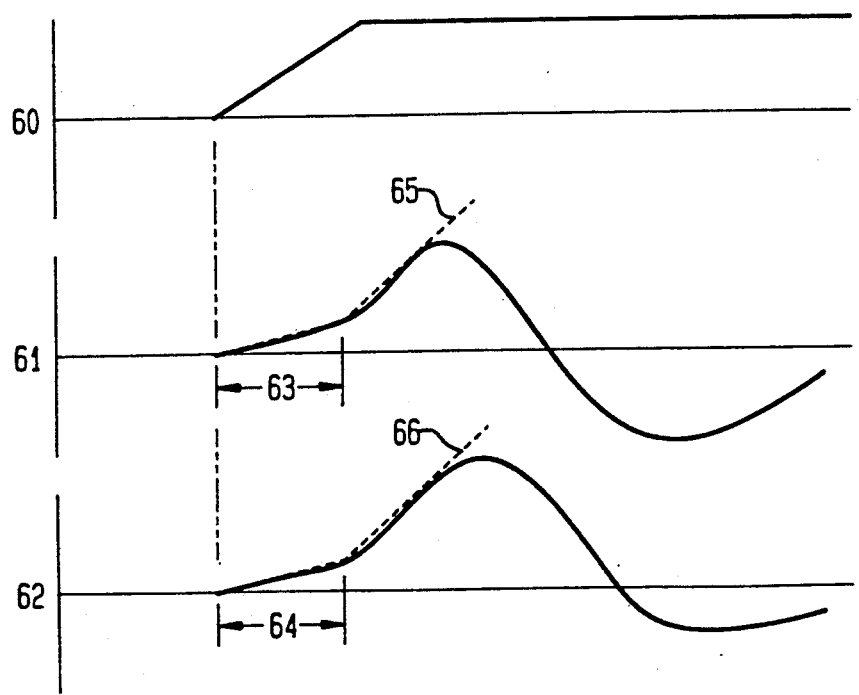
FIG. 6, in accordance with a preferred protocol of the present invention, shows a waveform of brief horizontal backward displacement of the support surface and corresponding trajectories of reaction force exerted by the right and left feet of a typical normal subject against the support surface.

FIG. 6 shows the preferred waveform of support surface linear horizontal displacement (60) along with typical support surface reaction forces (61 and 62) exerted by each of the two feet of a freely standing normal subject. In trace 60, the vertical axis shows displace (up is backward and down is forward) and the horizontal axis shows time. Traces 61 and 62 show front-back changes in position of the vertical force center (functionally related to torque exerted about the ankle joint axes) exerted by the right and left feet, respectively. In these traces, the vertical axes show vertical force center displacements (up is forward and down is backward), while the horizontal axes show time.

The onset time for the active force response of the right (63) and left (64) legs is indicated by the abrupt increase in the rate of change in anteroposterior position of the vertical force center against the support surface. This parameter of the active force response is called the Latency parameter. The force of muscular contraction for each leg is measured by the rate of change of the anteroposterior position of the vertical force center (65 and 66) following the abrupt onset of the active force response. This parameter of the active force response is called the Strength parameter.

Figure 7:
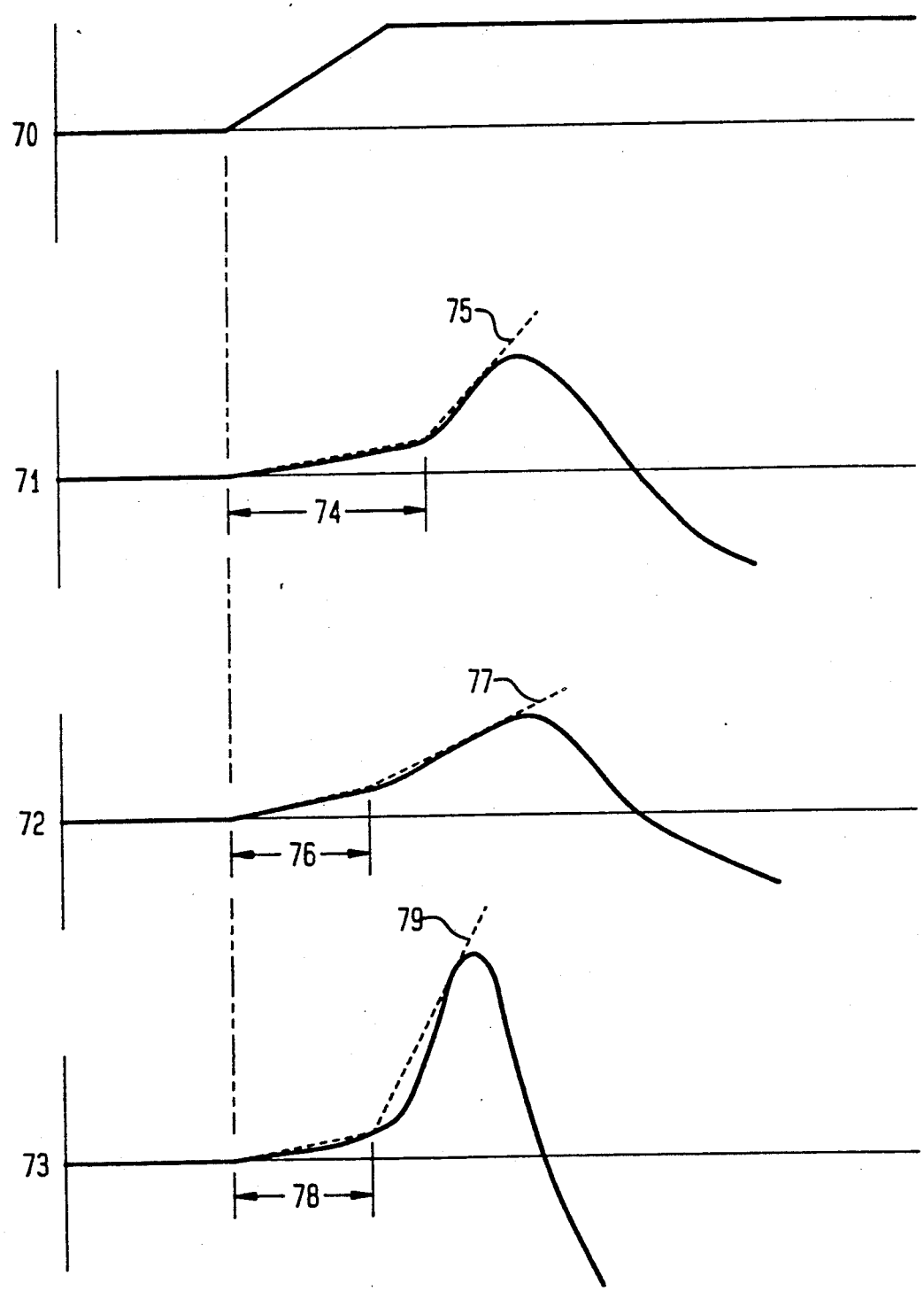
FIG. 7 uses the same format of FIG. 6 to illustrate abnormalities in active response Latency and Strength parameters, typical of the subject with disorders in the coordination of muscular responses.

FIG. 7 illustrates the types of response Latency and Strength abnormalities typical of motorically impaired patients. Trace 70 shows the brief waveform of backward horizontal support surface displacement, according to a preferred protocol of the present invention. Trace 71 shows the vertical force center changes of a leg in an individual with abnormally long response Latency (74) but normal response Strength (75). Trace 72 shows the vertical force center changes of a leg in an individual with normal response Latency (76) but abnormally small response Strength (77). Finally, trace 73 shows the vertical force center changes of a leg in an individual with abnormally long response Latency (78) and abnormally strong response Strength (79). By identifying normal and abnormal Latency and Strength parameters as a function of leg and perturbation direction, it is then possible to determine the distribution of postural movement abnormalities.

A system for categorizing a subject's ability to execute effective postural movements with the two legs is described in Table II. Categories of abnormality are described separately for Latency and Strength parameters. Categories are based on differences in the measured Latency and Strength values between the two legs and between the two directions (forward and backward) of horizontal, linear displacement, as well as on comparisons to parameters values established for age-matched normals. The significance of differences in parameter values between the two legs, two directions, and subject populations can be determined by statistical methods well-known in the prior art.

TABLE II

CATEGORIES FOR NORMAL AND ABNORMAL POSTURAL MOVEMENTS

| MOTOR TEST PROCEDURE | SURFACE REACTION FORCES OF LEGS | |
|---|---|---|
| | ONSET TIME | STRENGTH |
| LATENCY CATEGORIES | | |
| A. Delays Symmetric Laterally and Directionally | L/L = L/R > NORM; +L/L = −L/L and +L/R = −L/R | |
| B. Symmetric Laterally and Asymmetric Directionally | L/L = L/R; +L/L # −L/L and +L/R # −L/R | |
| C. Symmetric Directionally and Asymmetric Laterally | L/L # L/R; +L/L = −L/L and +L/R = −L/R | |
| D. Asymmetric Laterally and Directionally | L/L # L/R; +L/L # −L/L and/or +L/R # −L/R | |
| N. Normal Latencies | L/L = L/R = NORM | |
| STRENGTH CATEGORIES | | |
| A. Symmetric Laterally and Asymmetric Directionally | | S/L = S/R; +S/L # −S/L and +S/R # −S/R |
| B. Symmetric Directionally and Asymmetric Laterally | | S/L # S/R; +S/L = −S/L and +S/R = −SR |
| C. Asymmetric Laterally and Directionally | | S/L # S/R; +S/L # −S/L and/or +S/R # −S/R |

TABLE II-continued
CATEGORIES FOR NORMAL AND ABNORMAL POSTURAL MOVEMENTS

| MOTOR TEST | SURFACE REACTION FORCES OF LEGS | |
|---|---|---|
| PROCEDURE | ONSET TIME | STRENGTH |
| N. Normal Strengths | | S/L = S/R = NORM |

Legend:
L Latency parameter value
S Strength parameter value
L/R Latency parameter value right leg
+L/R Latency parameter value right leg forward direction
−S/L Strength parameter value left leg backward direction
= substantially equivalent parameter values
> parameter value substantially greater than
parameter values substantially different
NORM parameter value range for age-matched normals In accordance with my system for categorizing normal and abnormal postural movements, subjects are placed in Latency Category A whose active response latencies are substantially similar in the left and right legs and for the forward and backward perturbation directions, but in all instances are greater in value compared to the range of values established for an age-matched normal population. Subjects are placed in Latency Category B whose active force response latencies, for a given direction of perturbation, are substantially similar in the left and right legs, but substantially different within the same leg for the two directions of perturbation. Subjects are placed in Latency Category C whose active force response latencies, for a given leg, are substantially similar for the two directions of perturbation, but substantially different for both directions of perturbation between the two legs. Subjects are placed in Latency Category D whose active force response latencies differ substantially between the two legs, and also differ substantially within each leg between the two directions of perturbation. Subjects are placed in Latency Category N whose active force response latencies are substantially similar in the two legs and in the two directions, and in all instances substantially within the range of values established for an age-matched normal population.

Subjects are placed in Strength Category A whose active force response strengths, for a given direction of perturbation, are substantially similar in the left and right legs, but substantially different within the same leg for the two directions of perturbation. Subjects are placed in Strength Category B whose active force response strengths, for a given leg, are substantially similar for the two directions of perturbation, but substantially different for both directions of perturbation between the two legs. Subjects are placed in Strength Category C whose active force response strengths differ substantially between the two legs, and also differ substantially within each leg between the two directions of perturbation. Subjects are placed in Strength Category N whose active force response strengths are substantially similar in the two legs and in the two directions, and in all instances substantially within the range of values established for an age-matched normal population.

Figure 8:
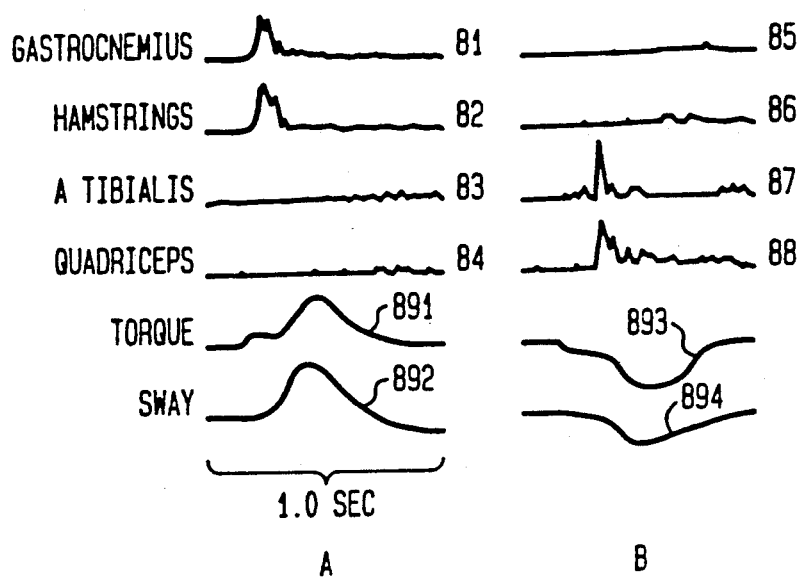
FIG. 8 depicts the electromyographic signal traces from the four indicated leg muscles of a subject standing upon a support surface according to the invention and subjected to forward or backward anteroposterior sway perturbation without "stabilization" of the support surface or the visual surround.

The temporal and spatial "Structure" of muscular contractions are distilled from EMG recordings, a typical normal example of which is shown in FIG. 8. This figure shows typical electromyographic traces from four leg muscles of a subject regaining equilibrium following a backward (traces 81-84) and forward (traces 85-88) horizontal displacement of the support surface. There are also plotted the restoring torques (891 and 893) and the angular amplitude of sway (892 and 894) of the subject over the corresponding one-second time interval following perturbation. This data permits a simple tabulation of the specific muscles involved in correcting forward (side A) and backward (side B) sway, the relative strength of such muscle responses, and the timing thereof. By techniques of graphic analysis, or direct computation from the underlying signal traces, this quantifying data may be quickly analyzed or displayed for comparison with corresponding data from other subject populations.

The ready compilation of this data further allows a more complete understanding of a given subject's visually observed postural response. For instance one may quickly distinguish the equilibrium which results from a subject's small but timely responses of appropriate muscles to small sway perturbations, as shown in FIG. 8, from an inappropriate contracting of all postural muscles of a subject lacking normal coordination. Under small perturbations, the general mechanical stiffening of the latter would result in a degree of stability which might appear clinically normal on simple visual inspection. The dynamic correlation of support motions, muscle signal traces and normal responses permits a quick differentiation of such conditions, and would promptly single out the abnormal subject in a clinical setting for appropriate further testing.

Figure 9:
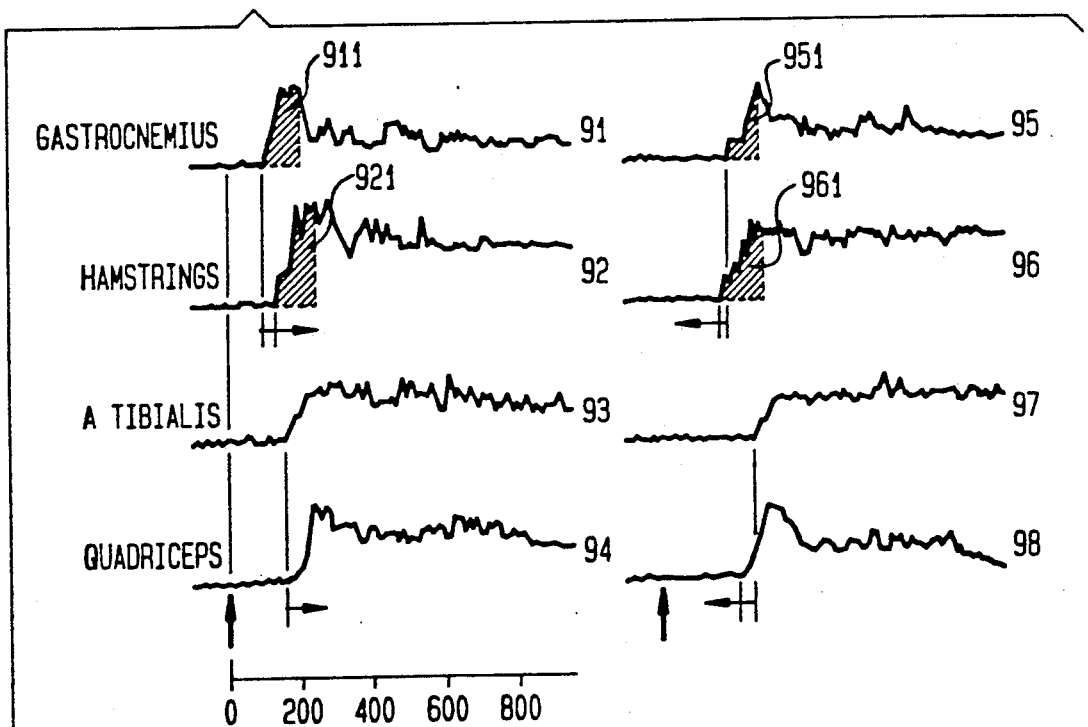
FIG. 9 depicts the electromyographic signal traces from four leg muscles in each leg of a spastic hemiplegic subject standing upon a support surface and caused to undergo anteroposterior sway by a backward support surface displacement according the invention.

Use of the invention for computing temporal and spatial parameters of muscle coordination is illustrated in FIG. 9 in which ensemble averaged EMG, torque, and AP sway records of the less-involved and the spastic legs in a spastic hemiplegic subject are compared in response to forward sway perturbations. Forward sway rotations of the body about the ankle joints were compensated in the less-involved leg by contractions of the stretching gastrocnemius muscle (record 91), latency 97+/−5 msec (mean+/−S.D.). Mechanically coupled motions of the hips were stabilized by contraction of the synergist hamstrings muscle (record 92) beginning on the average 26+/−12 msec (mean+/−S.D.) later than in the gastrocnemius. The sequence of muscle activation beginning distally at the base on support and radiating proximally away from the support is highlighted in FIG. 9 by the rightward pointing arrow relating the relative latencies of gastrocnemius and hamstrings muscles, while the relative strengths of gastrocnemius and hamstring contractions during the first 75 msec of response (numerical integral of EMG signals) are illustrated by the shaded areas 911 and 921 respectively. This temporal and spatial structuring the EMG response to forward sway perturbations is the same as that observed in normal adults and normal juveniles aged 1½ to 10 years.

The pattern of contraction within muscles of the spastic leg shown in FIG. 9 was significantly different than that described above. Latency of gastrocnemius response (record 95) was slower (145+/−13 msec), and the sequence of activity was temporally reversed beginning in the hamstrings (record 96) and then radiating distally towards the base of support as indicated by the negative sequence value (−31 +/−25 msec) and the leftward pointing arrow relating relative latencies of gastrocnemius and hamstrings muscles. Note that subsequent activation of the anterior tibialis (records 93 and 97) and quadriceps muscles (record 94 and 98), antagonists which helped brake the return sway movement, were sequenced in the non-involved leg beginning at base of support and then radiating upward, while the reverse sequence of antagonist activation was again observed in muscles of the spastic leg.

Methods of the present invention for quantifying, separately in the less-involved and in the spastic leg, three parameters of muscular coordination are introduced under the "Structure" heading below the EMG traces. In the parameterization of the temporal structuring of response, positive "timing" values (shown in item 901) of the less-involved leg indicate that activity commenced in the ankle joint muscles (closest to base of support) and then radiated proximally to the upper leg synergists. In contrast, the negative values of spastic leg (shown in item 902) contractions depict the opposite proximal to distal sequence of activation. In the parameterization of the spatial structuring of response, the standard deviation of the mean H/G ratio quantifies the degree of lixation in the relative activation strengths of distalproximal synergists during the initial 75 msec of response. Another spatial parameter, the T/G ratio, characterizes the level of co-activation of the antagonist ankle muscle during this interval of the response. Compared to the less-involved leg (open bars in item 903), the linkages between synergists in the spastic leg (shaded bars in item 904) were 3½ times more variable (larger S.D. of H/G ratio), and the level of coactivation of the antagonist was over twice as great (larger T/G ratio).

Similar results were obtained for this subject when subject to backward sway perturbations (support surface displaced forward). When parameters quantifying the temporal and spatial structure of automatic postural adjustments to such perturbations were distilled from the EMG records of the subject, the distribution of normal and abnormal parameters was identical to that shown in FIG. 9. Compared to the less involved leg, the temporal order of activation in the spastic leg was reversed, the linkage between synergists was much more variable, and the level of antagonist co-activation was greater.

It is possible to combine the Sense and Motor Test Procedures such that ability to utilize support surface inputs from one leg to execute postural movements in the other leg can be selectively assessed. This combination of test procedures is useful for identifying more subtle forms of abnormal sensory processing and movement coordination in those subjects whose Latency and Strength parameters are within the normal range (Category N) when both legs receive useful support surface inputs. These procedures are combined by repeating the Motor Test Procedure for Sense Test Procedure conditions 3 and 4. (Note that the Motor Test Procedure is normally run under Sense Test Procedure condition 1 only.) For each repetition of the Motor Test Procedure, methods identical to those described in FIGS. 6 and 7 and Table II are repeated to identify Latency and Strength categories as a function of the sensory test condition.

For those subjects whose Motor Test Procedure results show no asymmetries in Latency (category A or N) or Strength (category N) parameters, I establish an additional set of criteria for distinguishing among categories of normal and abnormal distribution of support surface inputs. Sensory Distribution categories are based on differences in Motor Test Procedure Latency and Strength categories between trials run under Sense Test Procedure conditions 1, 3, and 4. Again, statistical methods well-known in the prior art can be used to identify significant differences in parameter values. A system according to the present invention for establishing categories for normal and abnormal sensory distribution is shown in Table III.

TABLE III

CATEGORIES FOR NORMAL AND ABNORMAL
DISTRIBUTION OF SUPPORT SURFACE INPUTS

| DISTRIBUTION CATEGORIES | LATENCY AND STRENGTH CATEGORIES MOTOR TEST PROCEDURE | | |
|---|---|---|---|
| | Condition 1 | Condition 3 | Condition 4 |
| A. Abnormal Bilaterally | L & S = A,N | L or S = B,C,D | L or S = B,C,D |
| B. Normal Left to Right, Abnormal Right to Left | L & S = A,N | L & S = A,N | L or S = B,C,D |
| C. Normal Right to Left, Abnormal Left to Right | L & S = A,N | L or S = B,C,D | L & S = A,N |
| N. Normal Distribution | L & S = A,N | L & S = A,N | L & S = A,N |

Legend:
L Latency parameter
S Strength parameter
A B C D N Categories
= parameter is in category As described in Table III, a subject is placed in Sensory Distribution Category A (abnormal bilaterally) who shows no lateral or directional asymmetries in Latency and Strength (Motor Test categories A or N) when the Motor Test Procedure is applied under sensory condition 1 but shows either one or a combination of lateral and directional asymmetries (Motor Test categories B, C, or D) under both sensory condition 3 and condition 4 testing. A subject is placed in category B (sensory distribution abnormal right to left) who shows no lateral or directional asymmetries in Latency and Strength (Motor Test categories A or N) when the Motor Test Procedure is applied under sensory condition 1 and 3 but shows either one or a combination of lateral and directional asymmetries when the same procedure is applied under sensory condition 4. A subject is placed in category C (sensory distribution abnormal left to right) who shows no lateral or directional asymmetries in Latency and Strength (Motor Test categories A or N) when the Motor Test Procedure is applied under sensory condition 1 and 4 but shows either one or a combination of lateral and directional asymmetries when the same procedure is applied under sensory condition 3. Finally, a subject is placed in category N (normal sensory distribution) who shows no lateral or directional asymmetries in Latency and Strength (categories A or N) when the Motor Test Procedure is applied under sensory condition 1, 3, and 4.

Some subjects may be unable to maintain their standing equilibrium when the support surface of one foot is sway-referenced with a gain of unity. Therefore, it is sometimes necessary to modify the Sense Test Procedure with the sway-reference gains reduced from unity to a fraction. This modification provides the subject with poorer equilibrium the with sufficient support surface input information to remain standing. In other instances, the test can be made more challenging for the subject with exceptionally good equilibrium by increasing the sway-reference gains above unity.

It is also possible to modify the Sense Test Procedure such that a simpler device can be used to identify normal and abnormal parameters for receiving and correctly interpreting somatosensory orientation information. Either one support surface at a time or both surfaces simultaneously are made compliant about an axis of rotation co-linear with the ankle joints. Compliance is produced by restraining the rotational motion of the surface with a compliant element. The compliant element can have purely elastic properties, such as a spring, or a combination of elastic and viscous properties, such as a spring with fluid damper. Forces exerted by the supported leg against the support surface move the compliant element and thereby rotate the surface.

Figure 10:
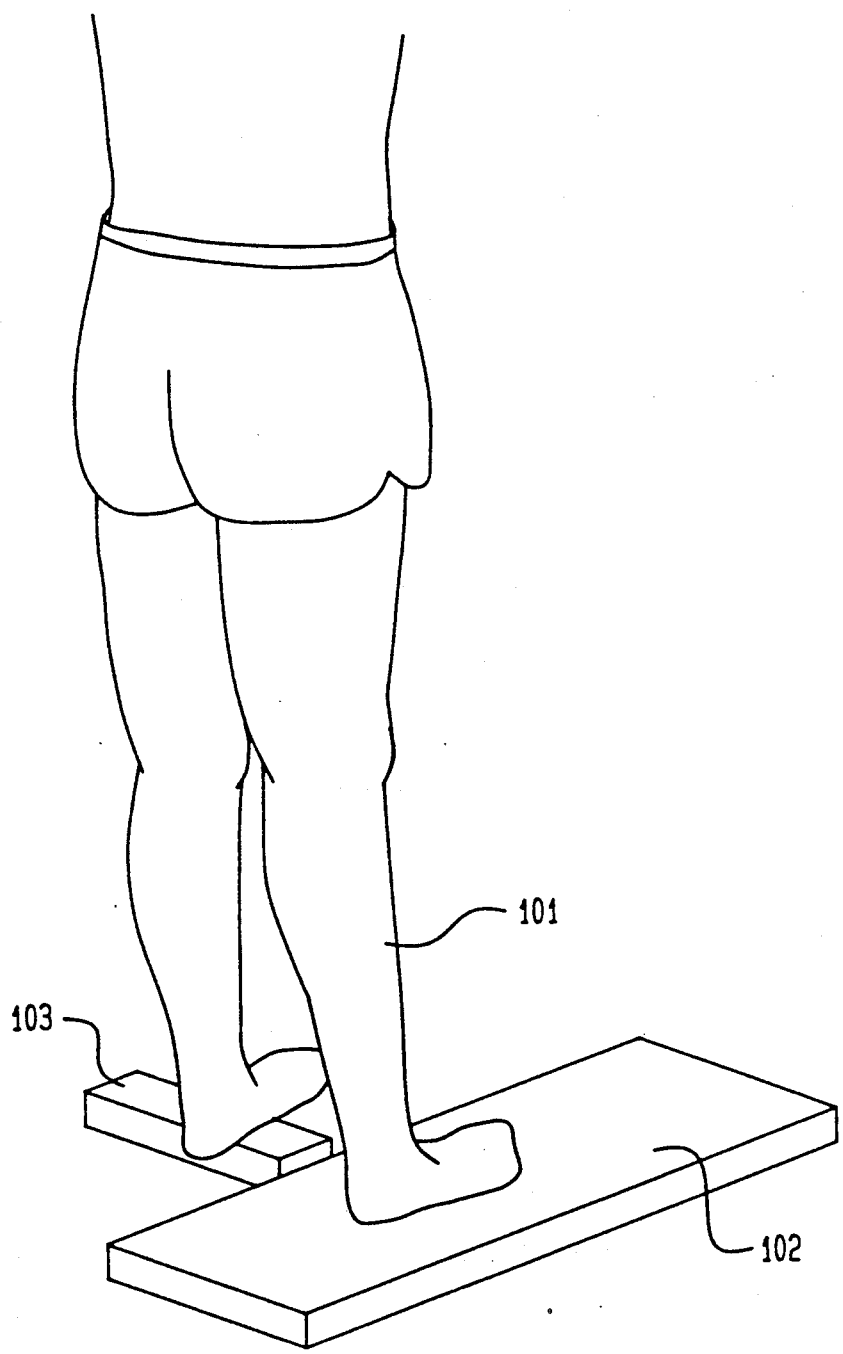
FIG. 10 shows a schematic representation of a simplified means according to the present invention for disrupting somatosensory orientation information useful for maintaining a standing position in equilibrium from one leg at a time.

It is possible to modify the Motor Test Procedure so that ability to execute postural movements is assessed while the subject relies on only one leg at a time to maintain balance. FIG. 10 shows an embodiment of a device according to the present invention in which the subject (101) assumes a standing position in equilibrium with one leg supported on a surface (102) longer than the foot is long, and the other leg on a surface (103) short in relation to foot length. This modification to the support surface configuration allows the subject to continue to bear weight equally with the two feet but prevents changes in the anteroposterior position of the center of vertical force (equivalent to exerting ankle torque) in the leg supported by the shortened support surface. By repeating the Motor Test Procedure with one foot at a time supported by a shortened support surface and by determining Latency and Strength parameter values for each leg, it is possible to re-apply the system for establishing categories for normal and abnormal postural movement control described in Table II.

Figure 2:
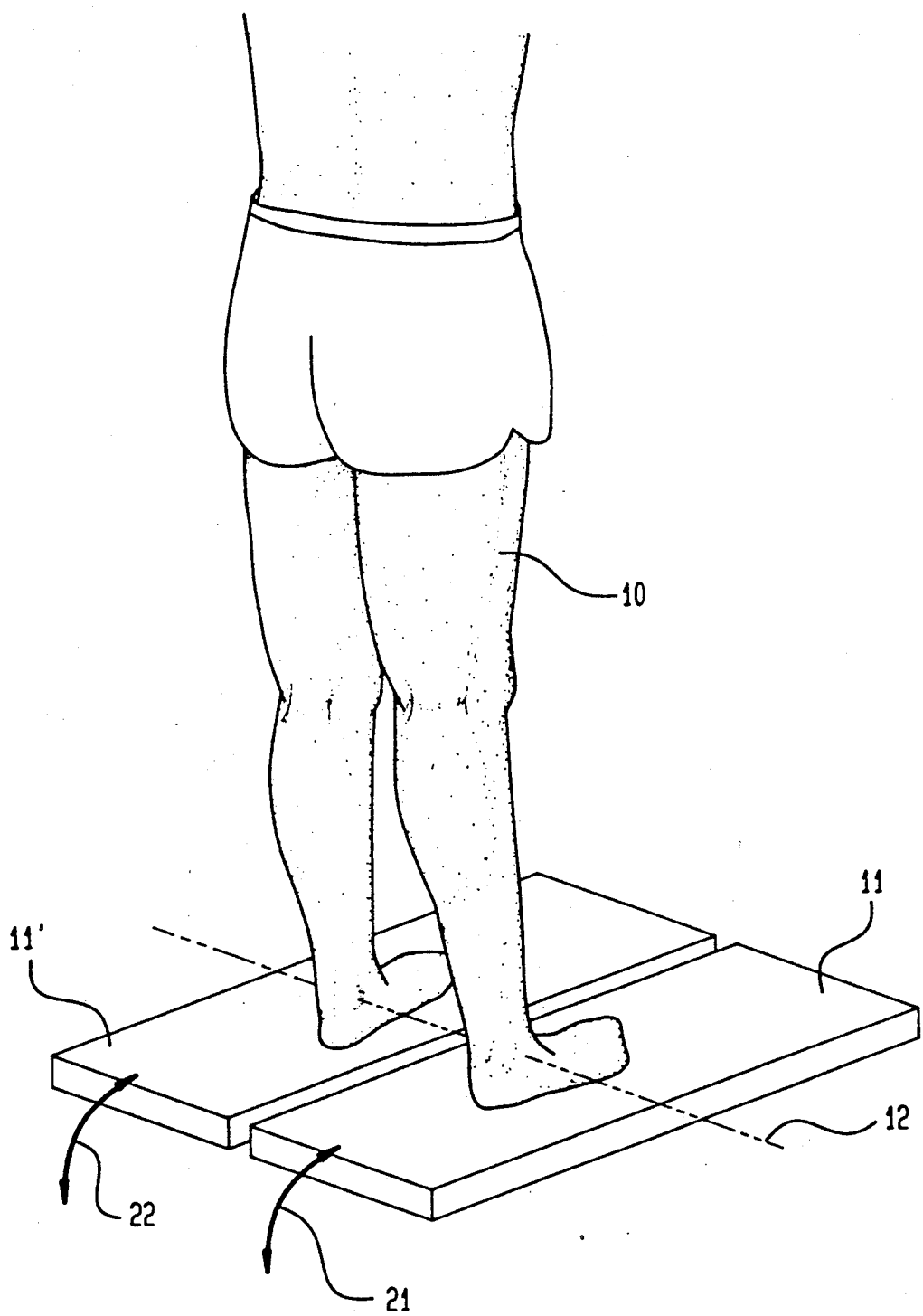
FIG. 2 shows the assumed standing equilibrium position of a subject with the right and left feet placed on two adjacent support surfaces.

It is further possible to modify the Motor Test Procedure so that ability to execute postural movements while the subject relies on one leg at a time is assessed, without modifying the support surface configuration. According to this embodiment of my invention, the subject assumes a position in equilibrium as shown in FIG. 2. The subject is instructed to step in-place by alternately raising one foot and then the other above the support surface. The subject is exposed to brief waveforms of support surface horizontal, linear displacement which coincide with phases of the in-place step cycle in which the subject is supported by one leg. The properties of the resulting postural movements produced by the supporting leg are measured and categorized using the same system for categorizing normal and abnormal postural movement control described in Table II.

A protocol implemented by the program means which I call the In-Place Stepping Motor Test Procedure includes the following procedures: (1) The subject assumes a standing position of equilibrium on two independent support surfaces. (2) The subject steps in-place. (3) A quantity related to the vertical force exerted by each leg against its support is measured and transmitted to the program means. (4) The program means, based on the vertical force measurements, identifies a time during which the subject is supported by one leg and, in accordance with a diagnostic protocol, transmits a command to the actuator means to produce a brief waveform of horizontal, linear support surface displacement. (5) The properties of the resulting postural movement back to equilibrium are determined by methods similar to those described for the Motor Test Protocol. (6) Steps 4 and 5 are repeated until measurements are made for all combinations of forward and backward directions of support surface horizontal, linear displacement and left and right leg support. (7) Latency and Strength parameter values are determined for each leg and for each displacement direction using methods similar to those described for the Motor Test Protocol. (8) Postural movements of the left and right legs are categorized according to criteria described in Table II.

Figure 11:
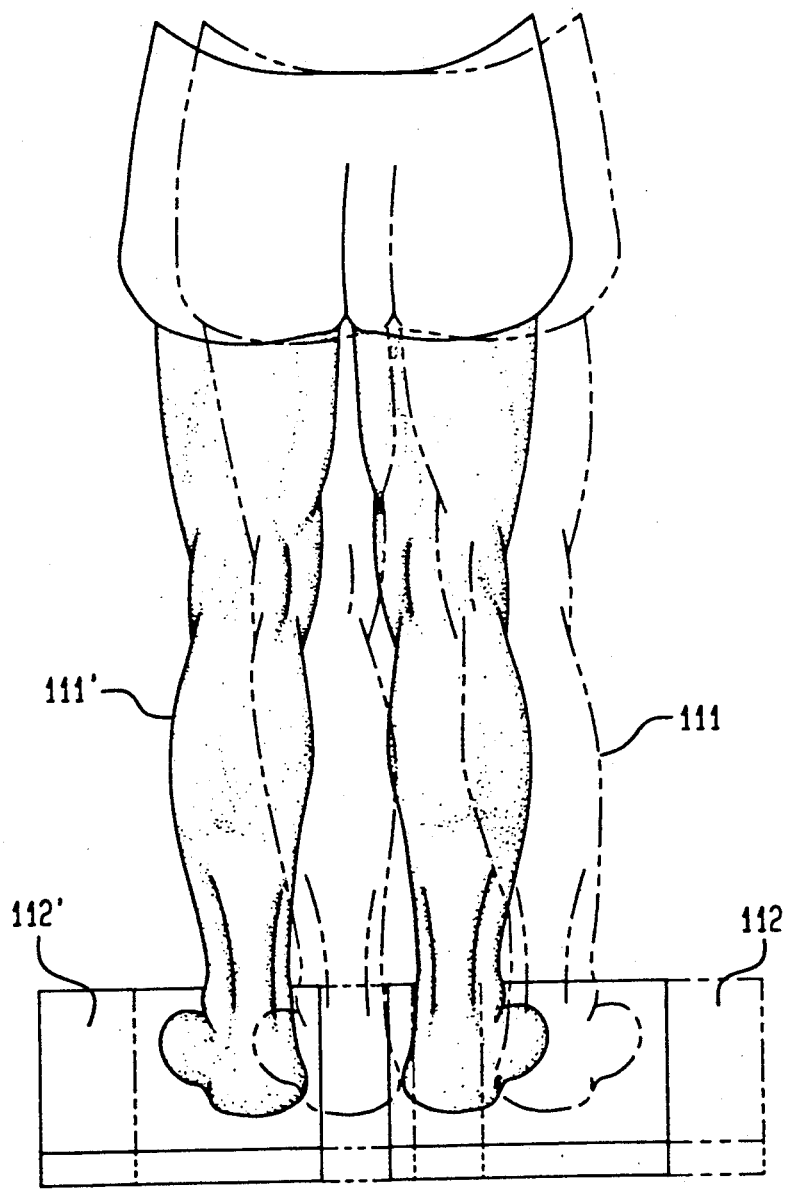
FIG. 11 shows a rear view of a subject maintaining an assumed equilibrium position on a support surface prior to and following a lateral linear displacement of the support surface.

It is possible to modify the Motor Test Procedure so that the ability of the subject to execute postural movements in the two legs can be separately assessed for postural movements in the lateral direction. This embodiment of my invention is shown in FIG. 11, which shows a rear view of a subject maintaining an assumed equilibrium position on a support surface prior to and following a lateral linear displacement of the support surface. Dotted lines show the position of the subject (111) and the support surface (112) prior to the linear displacement, and solid lines show the position of the subject (111') and the support surface (112') following the lateral horizontal, linear displacement. The subject stands perpendicular to the axis of support surface horizontal, linear displacement. A brief waveform of support surface horizontal, linear displacement in one lateral direction (from 112 to 112') displaces the body center of mass in the opposite lateral direction in relation to the support (from 111 to 111').

Figure 12:
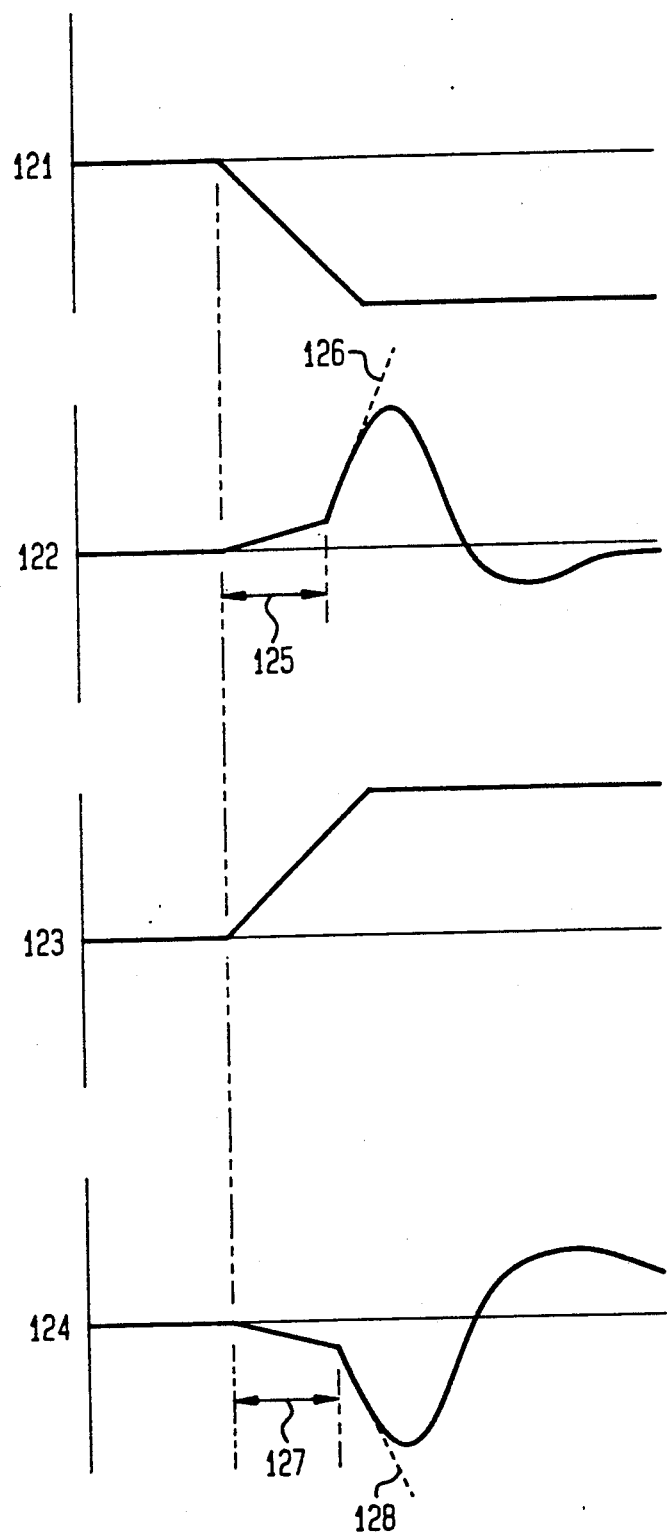
FIG. 12, in accordance with a preferred protocol of the present invention, shows a waveform of brief lateral horizontal, linear displacement of the support surface and corresponding trajectories of reaction force exerted by the feet of a typical normal subject against the support surface.

FIG. 12, in accordance with a preferred protocol of the present invention, shows a waveform of brief lateral horizontal, linear displacement of the support surface and corresponding trajectories of reaction force exerted by the feet of a typical normal subject against the support surface. The brief waveform of horizontal lateral support surface displacement is shown by traces 121 (leftward) and 123 (rightward). For these traces, the vertical axes show displacements (up is right and down is left) and the horizontal axis shows time. Traces 122 and 124 show changes in the lateral position of the vertical force center exerted by the right and left feet in response to leftward or rightward lateral horizontal, linear displacements, respectively. In these traces, the vertical axes show vertical force center displacements (up is right and down is left), while the horizontal axes show time. The Latencies of onset of the active force responses are shown for the leftward (125) and rightward (127) displacements. The Strengths of the active force responses are shown by the rates of increase in active force for the leftward (126) and rightward (128) displacements. Note that Latency (125 and 127) and Strength (126 and 128) parameters can be calculated for the left to right changes in position of the vertical force center using the same methods as with the records of front to back change in position of the vertical force center shown in FIG. 6.

It is possible in the Motor Test Procedure to use alternative means to produce brief anteroposterior and lateral displacements of the subject from the assumed equilibrium position. The subject can be instructed to grip a handle with one hand, and a brief waveform of horizontal, linear displacement of the handle produced. Alternatively, the subject can be instructed, on command, to pull or push against the handle.

Figure 13A:
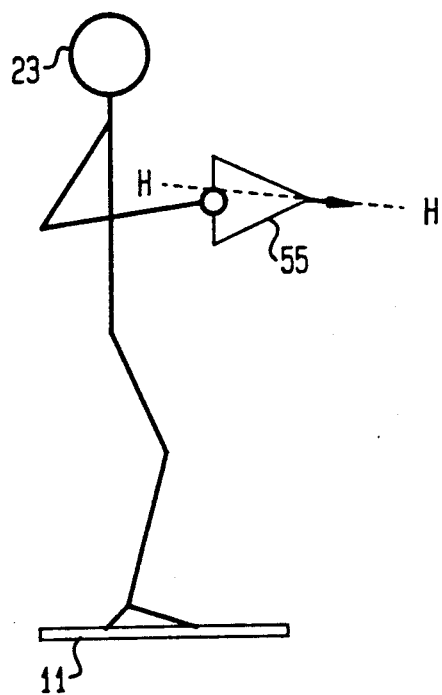
FIGS. 13A-13D show the use of a manipulandum in accordance with an embodiment of the invention, with the manipulandum positioned at the front or side of a subject standing or seated on the support surface.

Referring to FIG. 13A, the subject may be instructed to voluntarily pull or push upon the handle 55 upon the commencement of a tone. Such tone-triggered voluntary pulls and pushes are movements which displace the body center of mass forward and backward respectively, but in a manner accompanied by a very different configuration of sensory inputs in comparison to the horizontal, linear, translation of the support surface. Despite gross differences in the way postural adjustments were elicited in instances such as described in this paragraph, the coordination parameters can be determined using methods similar to those described in connection with the horizontal, linear, displacement perturbations.

Figure 13B:
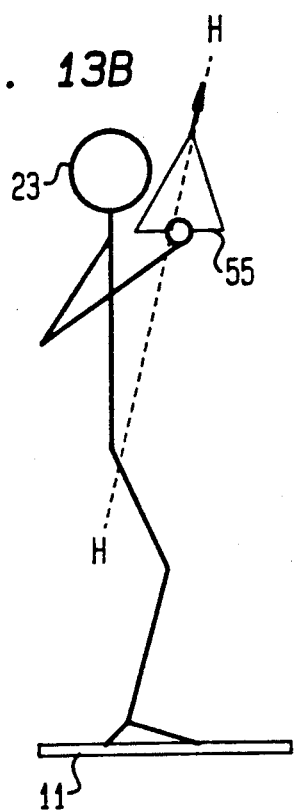
Figure 13C:
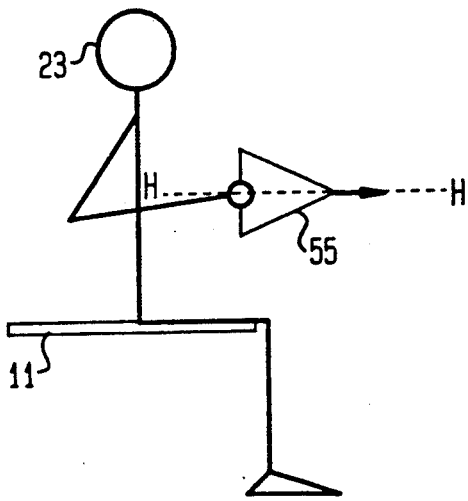
Figure 13D:
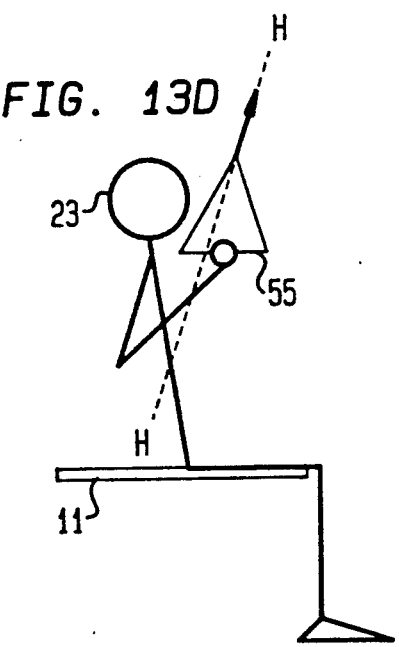

It will be appreciated that the invention may be used in a variety of applications in fashion analogous to that described above. For example, the manipulandum 55 shown in FIGS. 13A and 13C is being moved horizontally, as shown in FIGS. 13B and 13D in a plane orthogonal to the AP sway plane, i.e., laterally. Furthermore, although FIGS. 8 and 9 relate to use of leg muscles, muscles in the arm and other portions of the body may also be considered as postural muscles in appropriately created tests in a fashion analogous with the methods described above.

APPENDIX—LIST OF REFERENCES

1. Kandel, E. R., Schwartz, J. H. Principles of Neural Science. Elsevier/North-Holland, N.Y., 731 pp (1981).
2. Holt, K. S. Facts and fallacies about neuromuscular function in cerebral palsy as revealed by electromyography. Developmental Medicine and Child Neurology 8: 255-267 (1966).
3. Milner-Brown, H. S., Penn, R. D. Pathophysiological mechanisms in cerebral palsy. Journal of Neurology Neurosurgery Psychiatry 42: 606-618 (1979).
4. Sahrmann, S. A. Norton, B. J. The relationship of voluntary movement to spasticity in the upper motor neuron syndrome. Annals of Neurology 2: 460-465 (1977).
5. Arcan, M., Brull, M. A., Najenson, T., Solzi, P. FGP assessment of postural disorders during the process of rehabilitation. Scandinavian Journal of Rehabilitation Medicine 9: 165-168 (1977).
6. Black, F. O., Wall III, C., O'Leary, D. Computerized screening of the human vestibulospinal system. Annals of Otology Rhinology and Laryngology 87: 853-864 (1978).
7. Coats, A. C. The effect of varying stimulus parameters on the galvanic body-sway response. Annals of Otology 82: 96-105 (1973).
8. Dietz, V. Mauritz, K-H., Dichgans, J. Body oscillations in balancing due to segmental stretch reflex activity. Experimental Brain research 40: 89-95 (1980).
9. Njiokiktjien, C., de Rijke, W. The recording of the Romberg's test and its application of neurology. Agressology 13C; 1-7 (1972).
10. Diener, H. C., Dichgans, J., Bruzek, W., Selinka, H. Stabilization of the human posture during induced oscillations of the body. Experimental Brain research 45: 126-132 (1982).
11. Gurfinkel, V. S., Lipshits, M. I., Popov, K. Y. Is the stretch reflex the main mechanism in the system of regulation of the vertical posture of man? Biophysics 19: 744-748 (1974).
12. Nashner, L. M. A model describing the vestibular detection of body sway motion. Acta Otolaryngologica (Stockh) 72: 429-436 (1971).
13. Nashner, L. M. Vestibular posture control model. Kybernetik 10: 106-110 (1972).
14. Nashner, L. M. Adapting reflexes controlling the human posture. Experimental Brain Research 26: 59-72 (1976).
15. Nashner, L. M. Fixed patterns of rapid postural responses among leg muscles during stance. Experimental Brain Research 30: 13-24 (1977).
16. Nashner, L. M., Cordo, P. J. Relation of postural responses and reaction-time voluntary movements in human leg muscles. Experimental Brain Research 43: 395-405 (1981).
17. Nashner, L. M., Woollacott, M., Tuma, G. Organization of rapid response to postural and locomotor-like perturbations of standing man. Experimental Brain Research 36; 463-476 (1979).
18. Nashner, L. M., Shumway-Cook, A., Marin, O. Stance posture control in select groups of children with cerebral palsy: deficits in sensory organization and muscular coordination. Experimental Brain Research 49: 393-409 (1983).
19. Dietz, V., Berger, W. Spinal coordination of bilateral leg muscle activity during balancing. Experimental Brain Research 47: 172-176 (1982).
20. Nashner, L. M. Balance adjustments of humans perturbed while walking. Journal of Neurophysiology 44: 650-664 (1980).
21. Diener, H. C., Dichgans, J., Bacher, M., Gompf, B. Quantification of postural sway in patients with cerebellar diseases. Electroecephalography and Clinical Neurophysiology 57: 134-142 (1984).
22. Diener, H. C., Dichgans, J., Bootz, F., Bacher, M. Early stabilization of human posture after a sudden disturbance; influence of rate and amplitude of displacement. Experimental Brain Research 56: 126-134 (1984).
23. Berger, W., Dietz, V., Quintern, J. Corrective reactions to stumbling in man: neuronal coordination of bilateral leg muscle activity during gait. Journal of Physiology (Lond) 357: (1984).
24. Nashner, L. M., Forssberg, H. The phase dependent organization of postural adjustments associated with arm movements while walking. Journal of Neurophysiology : (1986).
25. Terekhov, Y. Stabilomotry and some aspects of its applications: a review Biomedical Engineering 11: 12-15 (1976).
26. Tokita, T., Miyate, H., Fujiwara, H. Postural response induced by horizontal sway of a platform Acta Otolaryngologica Suppl 406: 120-124 (1984).
27. Nashner, L. M. Sensory Feedback in Human Posture Control. Massachusetts Institute of Technology Report MVT 70-3 (1970).

What is claimed is:

1. A method for selectively assessing in one body or limb part at a time a subject's ability to receive and correctly interpret somatosensory orientation information, such method comprising:
    A. placing the subject on a plurality of independent support surfaces, each surface supporting a different body or limb part of the subject, and having the subject assume a position of equilibrium thereon;
B. configuring the support surfaces in such a way that each may move in functional relation to the subject's displacement from the assumed equilibrium position, and permitting all but one of such support surfaces thus to move;
C. recording the extent of spontaneous displacements of the subject from the assumed equilibrium position;
D. successively repeating steps B and C in each case with a different support surface being the one that is not permitted to move, until all support surfaces have been selected in turn for exclusion from moving;
E. comparing the recorded spontaneous displacement for the support surface configurations generated in step B to each other; and
F. comparing, for each support surface configuration generated in step B, the recorded spontaneous displacements to a range of spontaneous displacements for normal individuals on a similar support surface configuration.

2. A method for selectively assessing in one body or limb part at a time the following substrates of posture control, the two substrates being (1) ability to receive and correctly interpret peripheral somatosensory orientation information for sensing displacements from an assumed equilibrium position and (2) ability to execute postural movements with the supported body or limb part for re-establishing the assumed equilibrium position following a brief transient perturbation therefrom, such method comprising:
A. placing the subject on a plurality of independent support surfaces and having the subject assume a position of equilibrium thereon;
B. measuring at least one quantity related to the subject's displacement from the assumed equilibrium position;
C. moving on a continuous basis a combination of the support surfaces in functional relation to the measured quantity, the combination being a number equal to or greater than no surfaces up to and including all the surfaces;
D. recording the extent of spontaneous displacements of the subject from the assumed equilibrium position;
E. perturbing on a brief transient basis the subject from the assumed position in equilibrium;
F. measuring quantities related to the active forces exerted by supported body and limb parts against the supporting surfaces and quantities related to the contractile activities of a plurality of body and limb part muscles providing postural support in response to the brief transient perturbations;
G. repeating procedures C, D, E, and F with differing, portions of the support surfaces fixed and moving in functional relation to the measured quantity;
H. comparing, for different portions of support surfaces fixed and moving in functional relation to the measured quantity, the following quantities:
H1. the extent of spontaneous displacements of the subject from the assumed equilibrium position
H2. the properties of the active forces generated by each supported body and limb part against its support surface in response to perturbation from the assumed equilibrium position
H3. the timing and structural properties of the contractile activities of the supporting muscles in response to perturbation from the assumed equilibrium position; and
I. applying a standardized protocol to distinguish among normal and abnormal categories for receiving and correctly interpreting peripheral somatosensory orientation information and for executing postural movements against the support surface based on the measured quantities.

3. A method according to claim 2, wherein step A includes the additional step of obstructing the subject's vision.

4. A method for selectively assessing in one supporting leg at a time the following substrates of standing posture control, the two substrates being (1) ability to receive and correctly interpret peripheral somatosensory orientation information for sensing displacements from an assumed equilibrium position and (2) ability to execute postural movements for re-establishing an assumed standing equilibrium position following a brief transient perturbation therefrom, such method comprising:
A. standing the subject with one foot on each of two independently movable support surfaces;
B. measuring at least one quantity related to the subject's displacement from the standing equilibrium position;
C. moving on a continuous basis a combination of the two support surfaces in functional relation to the measured quantity, the combination being a number equal to or greater than no surfaces up to and including both surfaces, there being four possible combinations;
D. recording the extent of spontaneous displacements of the subject's center of body mass from the assumed equilibrium position;
E. perturbing on a brief transient basis the subject from the standing position in equilibrium;
F. measuring quantities related to the active forces exerted by each leg against its supporting surface and quantities related to the contractile activities of a plurality of leg muscles providing postural support in response to the brief transient perturbations;
G. repeating procedures C, D, E, and F with each of the four combinations of the two support surfaces fixed and moving in functional relation to the measured quantity;
H. comparing, for each of the four possible combinations of support surfaces fixed and moving in functional relation to the measured quantity, the following quantities:
H1. the extent of spontaneous displacements of the subject from the assumed equilibrium position
H2. the properties of active forces generated by each leg against its support surface in response to the perturbation
H3. the timing and structural properties of the contractile activities of a plurality of supporting leg muscles in response to the perturbation; and
I. applying a standardized protocol to distinguish among normal and abnormal categories for receiving and correctly interpreting peripheral somatosensory orientation information and for executing postural movements against the support surface based on the measured quantities.

5. A method according to claim 4, for selectively assessing in one supporting leg at a time the following substrates of standing posture control, the two substrates being (1) ability to receive and correctly interpret peripheral somatosensory orientation information for sensing displacements from an assumed equilibrium position and (2) ability to execute postural movements for re-establishing an assumed standing equilibrium position following a brief transient perturbation therefrom, wherein step A includes the additional step of obstructing the subject's vision.

6. A method, using actively movable support surfaces, for selectively assessing in one supporting leg at a time the ability to receive and correctly interpret peripheral somatosensory orientation information for sensing displacements from a standing equilibrium position in the anteroposterior plane of motion (hereinafter termed AP stance support surface inputs), such method comprising:

A. standing the subject with one foot on each of two adjacent support surfaces, each of which is independently rotatable about an axis (hereinafter termed support surface rotation axis) co-linear with the subject's ankle joints;

B. measuring at least one quantity related to the angular displacement of the subject's center of body mass in the anteroposterior direction from the standing equilibrium position (hereinafter termed AP stance orientation angle);

C. performing the Sensory Test Procedure as follows:

C1. fixing both support surfaces

C2. recording the extent of spontaneous changes in AP stance orientation angle over an interval of time C3. fixing the right leg support surface and rotating on a continuous basis the left leg support surface in relation to the AP stance orientation angle C4. recording the extent of spontaneous changes in AP stance orientation angle over an interval of time C5. fixing the left leg support surface and rotating the right leg support surface on a continuous basis in relation to the AP stance orientation angle C6. recording the extent of spontaneous changes in AP stance orientation angle over an interval of time C7. rotating on a continuous basis both support surfaces in relation to the AP stance orientation angle C8. recording the extent of spontaneous changes in the AP stance orientation angle;

D. applying a standardized protocol for categorizing as normal and abnormal the subjects ability to receive and correctly interpret AP support surface inputs selectively from each of the two leg as follows:

D1. placing a subject in Sense Category A whose spontaneous changes in AP stance orientation angle are substantially the same as one another and significantly greater than those of an age-matched normal population with both support surfaces fixed and with either one but not both of the surfaces rotating in functional relation to the AP stance orientation angle D2. placing a subject in Sense Category B whose spontaneous changes in AP stance orientation angle are substantially similar to one another and to those of age-matched normals with both support surfaces fixed and with one but not the other support surface rotating in functional relation to the AP stance orientation angle D3. placing a subject in Sense Category N whose spontaneous changes in AP stance orientation angle are substantially similar to one another and to those of an age-matched normal population when both support surfaces are fixed and with either one of the support surfaces rotated in relation to the AP stance orientation angle.

7. A method, using passively compliant support surfaces, for selectively assessing in one supporting leg at a time the ability to receive and correctly interpret peripheral somatosensory orientation information for sensing displacements from the standing equilibrium position in the anteroposterior plane of motion (hereinafter termed AP stance support surface inputs), such method comprising:

A. standing the subject with one foot on each of two adjacent support surfaces, each of which is independently rotatable about an axis (hereinafter termed support surface rotation axis) co-linear with the subject's ankle joints;

B. measuring at least one quantity related to the AP stance orientation angle;

C. performing the Sensory Test Procedure as follows:

C1. fixing both support surfaces

C2. recording the extent of spontaneous changes in AP stance orientation angle over an interval of time C3. fixing the right leg support surface and making the left leg support surface compliant to changes in angle about the support surface rotation axis C4. recording the extent of spontaneous changes in AP stance orientation angle over an interval of time C5. fixing the left leg support surface and making the right leg support surface compliant to changes in angle about the support surface rotation axis C6. recording the extent of spontaneous changes in AP stance orientation angle over an interval of time C7. making both support surfaces compliant to changes in angle about the support surface rotation axis C8. recording the extent of spontaneous changes in the AP stance orientation angle;

D. applying a standardized protocol for categorizing as normal and abnormal the subjects ability to receive and correctly interpret AP support surface inputs selectively from each of the two leg as follows:

D1. placing a subject in Sense Category A whose spontaneous changes in AP stance orientation angle are substantially the same as one another and significantly greater than those of an age-matched normal population with both support surfaces fixed and with either one but not both of the surfaces compliant to changes in angle about the support surface rotation axis D2. placing a subject in Sense Category B whose spontaneous changes in AP stance orientation angle are substantially similar to one another and to those of age-matched normals with both support surfaces fixed and with one but not the other support surface compliant to changes in angle about the support surface rotation axis D3. placing a subject in Sense Category N whose spontaneous changes in AP stance orientation angle are substantially similar to one another and to those of an age-matched normal population when both support surfaces are fixed and with either one of the support surfaces compliant to changes in angle about the support surface rotation axis.

* * * * *